United States Patent
Wang et al.

(10) Patent No.: US 7,177,021 B2
(45) Date of Patent: Feb. 13, 2007

(54) INTEGRATED RADIATION SOURCES AND AMPLIFYING STRUCTURES, AND METHODS OF USING THE SAME

(75) Inventors: Shih-Yuan Wang, Palo Alto, CA (US); M. Saif Islam, Mountain View, CA (US); Zhiyong Li, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 324 days.

(21) Appl. No.: 10/942,004

(22) Filed: Sep. 14, 2004

(65) Prior Publication Data

US 2006/0056463 A1   Mar. 16, 2006

(51) Int. Cl.
*G01J 3/44* (2006.01)
*G01N 21/65* (2006.01)

(52) U.S. Cl. .................................................. 356/301
(58) Field of Classification Search ................. 356/301
See application file for complete search history.

(56) References Cited

U.S. PATENT DOCUMENTS

| | | | |
|---|---|---|---|
| 4,547,801 A | 10/1985 | Haisma et al. |
| 4,674,878 A | 6/1987 | Vo-Dinh |
| 5,017,007 A | 5/1991 | Milne et al. |
| 5,187,461 A | 2/1993 | Brommer et al. |
| 5,216,686 A | 6/1993 | Holm et al. |
| 5,255,067 A | 10/1993 | Carrabba et al. |
| 5,256,596 A | 10/1993 | Ackley et al. |
| 5,265,106 A | 11/1993 | Garcia et al. |
| 5,293,392 A | 3/1994 | Shieh et al. |
| 5,317,587 A | 5/1994 | Ackley et al. |
| 5,335,240 A | 8/1994 | Ho et al. |
| 5,359,618 A | 10/1994 | Lebby et al. |
| 5,440,421 A | 8/1995 | Fan et al. |
| 5,468,656 A | 11/1995 | Shieh et al. |
| 5,471,180 A | 11/1995 | Brommer et al. |
| 5,527,712 A | 6/1996 | Sheehy |
| 5,600,483 A | 2/1997 | Fan et al. |
| 5,609,907 A | 3/1997 | Natan |
| 5,677,924 A | 10/1997 | Bestwick |
| 5,682,401 A | 10/1997 | Joannopoulos et al. |
| 5,684,817 A | 11/1997 | Houdre et al. |
| 5,706,306 A | 1/1998 | Jiang et al. |
| 5,739,945 A | 4/1998 | Tayebati |
| 5,771,253 A | 6/1998 | Chang-Hasnain et al. |
| 5,774,485 A | 6/1998 | Stein |
| 5,784,400 A | 7/1998 | Joannopoulos et al. |
| 5,837,552 A | 11/1998 | Cotton et al. |
| 5,990,850 A | 11/1999 | Brown et al. |
| 5,997,795 A | 12/1999 | Danforth et al. |

(Continued)

OTHER PUBLICATIONS

Blanco, Alvaro, et al., "Large-scale synthesis of a silicon photonic crystal with a complete three-dimensional bandgap near 1.5 micrometres," Letters to Nature, Nature, vol. 405, May 25, 2000, pp. 437-440.

(Continued)

*Primary Examiner*—F. L. Evans

(57) ABSTRACT

Integrated radiation source/amplifying structures for use in surface enhanced Raman spectroscopy (SERS) and hyper-SERS are disclosed. The structures include a radiation source integrated with a SERS-active structure that is provided within a resonant cavity. SERS and hyper-SERS systems employing the integrated radiation source/amplifying structures are disclosed. Methods of performing SERS and hyper-SERS are also disclosed.

40 Claims, 8 Drawing Sheets

U.S. PATENT DOCUMENTS

| | | | |
|---|---|---|---|
| 5,998,298 | A | 12/1999 | Fleming et al. |
| 6,058,127 | A | 5/2000 | Joannopoulos et al. |
| 6,134,043 | A | 10/2000 | Johnson et al. |
| 6,141,360 | A | 10/2000 | Kinugawa et al. |
| 6,149,868 | A | 11/2000 | Natan et al. |
| 6,154,591 | A | 11/2000 | Kershaw |
| 6,274,293 | B1 | 8/2001 | Gupta et al. |
| 6,339,030 | B1 | 1/2002 | Constant et al. |
| 6,396,083 | B1 | 5/2002 | Ortiz et al. |
| 6,406,777 | B1 | 6/2002 | Boss et al. |
| 6,434,180 | B1 | 8/2002 | Cunningham |
| 6,525,880 | B2 | 2/2003 | Flanders et al. |
| 6,546,029 | B2 | 4/2003 | Sirbu et al. |
| 6,608,685 | B2 | 8/2003 | Wood et al. |
| 6,608,716 | B1 | 8/2003 | Armstrong et al. |
| 6,623,977 | B1 | 9/2003 | Farquharson et al. |
| 6,649,683 | B2 | 11/2003 | Bell |
| 6,650,675 | B2 | 11/2003 | Sahara et al. |
| 6,678,289 | B2 | 1/2004 | Kim |
| 6,700,910 | B1 | 3/2004 | Aoki et al. |
| 6,711,200 | B1 | 3/2004 | Scherer et al. |
| 2002/0142480 | A1 | 10/2002 | Natan |
| 2002/0182716 | A1 | 12/2002 | Weisbuch et al. |
| 2003/0120137 | A1 | 6/2003 | Pawluczyk |
| 2004/0142484 | A1 | 7/2004 | Berlin et al. |
| 2004/0150818 | A1 | 8/2004 | Armstong et al. |

OTHER PUBLICATIONS

Campbell, M., et al., "Fabrication of photonic crystals for the visible spectrum by holographic lithography," Letters to Nature, Nature, vol. 404, Mar. 2, 2000, pp. 53-56.

Chang-Hasnain, Connie J., "Tunable VCSEL," IEEE Journal on Selected Topics in Quantum Electronics, vol. 6, No. 6, Nov./Dec. 2000, pp. 978-987.

Emory, Steven R., et al., "Screening and Enrichment of Metal Nanoparticles with Novel Optical Properties," J. Phys. Chem. B, 1998, 102, pp. 493-497.

Joannopoulos, J.D., et al., "Photonic crystals: putting a new twist on light," Nature, vol. 386, Mar. 13, 1997, pp. 143-149.

Johnson, Steven G., et al., Introduction to Photonic Crystals: Block's Theorem, Band Diagrams, and Gaps (But No Defects), Feb. 3, 2003, pp. 1-16.

Kneipp, Katrin, et al., Single Molecule Detection Using Surface-Enhanced Raman Scattering (SERS), Physical Review Letters, vol. 78, No. 9, Mar. 3, 1997, pp. 1667-1670.

Lalanne, Ph., et al., "Two physical mechanisms for boosting the quality factor to cavity volume ratio of photonic crystal microcavities," Optics Express, Feb. 9, 2004, vol. 12, No. 3, pp. 458-467.

Michaels, Amy M., et al., "Surface Enhanced Raman Spectroscopy of Individual Rhodamine 6G Molecules on Large Ag Nanocrystals," J. Am. Chem. Soc., 1999, 121, pp. 9932-9939.

Qi, Minghao, et al., "A three-dimensional optical photonic crystal with designed point defects," Letters to Nature, Nature, vol. 429, Jun. 3, 2004, pp. 538-542.

Tao, Andrea, et al., "Langmuir-Blodgett Silver Nanowire Momolayers for Molecular Sensing Using Surface-Enhanced Raman Spectroscopy," Nano Letters, vol. 3, No. 9, 2003, pp. 1229-1233.

Vlasov, Yuril A., et al., "On-chip natural assembly of silicon photonic bandgap crystals," Letters to Nature, Nature, vol. 414, Nov. 15, 2001, pp. 289-293.

Fainstein, A et al—"Raman Scattering Enhancement by Optical Confinement in a Semiconductor Planar Microcavity" —Phys Rev Lett vol. 75 Nov. 13, 1995.

Yao, J L et al—"A Complementary Study of Surface-Enhanced Raman Scattering and Metal Nanorod Arrays" —Pure & Applied Chemistry 2000 pp. 221-228.

INTEGRATED RADIATION SOURCES AND AMPLIFYING STRUCTURES, AND METHODS OF USING THE SAME

FIELD OF THE INVENTION

The present invention relates to Raman spectroscopy chemical analysis. More particularly, the present invention relates to integrated excitation radiation sources and radiation amplifying structures for use in surface enhanced Raman spectroscopy, systems employing such structures, and methods for performing surface-enhanced Raman spectroscopy (SERS) and hyper-SERS where the Raman radiation is roughly twice the frequency of the pumping radiation.

BACKGROUND OF THE INVENTION

Raman spectroscopy is a well-known spectroscopic technique for performing chemical analysis. In conventional Raman spectroscopy, high intensity monochromatic light provided by a light source, such as a laser, is directed onto an analyte (or sample) that is to be chemically analyzed. The analyte may contain a single molecular species or mixtures of different molecular species. Furthermore, Raman spectroscopy may be performed on a number of different types of molecular configurations, such as organic and inorganic molecules in either crystalline or amorphous states.

The majority of the incident photons of the light are elastically scattered by the analyte molecule. In other words, the scattered photons have the same frequency and, thus, the same energy (and, therefore, the same frequency, wavelength, or wavenumber), as the photons that were incident on the analyte. However, a small fraction of the photons (i.e., 1 in $10^7$ photons) are inelastically scattered by the analyte molecule. These inelastically scattered photons have a different energy than the incident photons. This inelastic scattering of photons is termed the "Raman effect." The inelastically scattered photons may have frequencies greater than or, more typically, less than the frequency of the incident photons. When an incident photon collides with a molecule, energy may be transferred from the photon to the molecule or from the molecule to the photon. When energy is transferred from the photon to the molecule, the scattered photon will then emerge from the sample having a lower energy and a corresponding lower frequency. These lower-energy Raman scattered photons are commonly referred to in Raman spectroscopy as the "Stokes radiation." A small fraction of the analyte molecules may be in an energetically excited state before an incident photon collides with the molecules. When an incident photon collides with an excited molecule, energy may be transferred from the molecule to the photon, which will then emerge from the sample having a higher energy and a corresponding higher frequency than the incident photon. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). By plotting the frequency of the inelastically scattered Raman photons against intensity, a unique Raman spectrum is obtained, which corresponds to the particular analyte. This Raman spectrum may be used for many purposes, such as identifying chemical species, identifying chemical states or bonding of atoms and molecules, and determining physical and chemical properties of the analyte.

Since the intensity of the Raman scattered photons is low, intense laser light sources are typically employed to provide the excitation radiation. Surface enhanced Raman spectroscopy (SERS) is another Raman spectroscopy technique that has been developed to increase the Raman signal produced by an analyte and to allow surface studies of an analyte. In SERS, analyte molecules are adsorbed onto or positioned near a specially prepared metal surface. Typically, the metal surface is made from gold, silver, copper, platinum, or aluminum. The intensity of the Raman scattered photons from a molecule adsorbed on such a metal surface is typically about $10^4$–$10^6$ greater than conventional Raman Spectroscopy and can be as high as $10^8$–$10^{14}$. In other words, more photons are inelastically scattered by the analyte molecules in SERS compared to conventional Raman spectroscopy.

The surface enhancement of the Raman signal in SERS is currently attributed to two primary mechanisms: electromagnetic field enhancement and chemical enhancement. The enhancement of the Raman signal is at least partially dependent on the surface roughness or surface features of the metal surface. In SERS, a strong electromagnetic field is present in the areas adjacent to and near the metallic surface when the surface is irradiated by the excitation radiation. This electromagnetic field is experienced by the analyte molecules adjacent to the surface. This strong electromagnetic field enhances the Raman signal emitted from the analyte, which is, at least in part, proportional to the square of the enhanced electromagnetic field. Thus, SERS may be used to perform, for example, surface studies and studies of material monolayers adsorbed on metals. While SERS is an effective chemical analysis tool, it requires rather large and powerful laser light sources. A typical SERS system occupies a large table and is not particularly portable.

Accordingly, there is a need for a more compact and portable SERS system. There is also a need for an excitation radiation source that requires less power during operation that also will enhance, simultaneously, the intensity of the Raman signal to enable more sensitive chemical analysis.

BRIEF SUMMARY OF THE INVENTION

An integrated radiation source/amplifying structure is disclosed that includes a first portion having a first surface and an opposing second surface, and a second portion having a face opposing the first surface of the first portion with a resonant cavity provided therebetween. A SERS-active structure is disposed between the first portion and the second portion within the resonant cavity. The integrated radiation source/amplifying structure also includes a radiation source configured to irradiate the SERS-active portion.

A surface enhanced Raman spectroscopy (SERS) system is disclosed that includes an integrated radiation source/amplifying structure and a detector. Additional optical equipment may also be used with the SERS system.

A method of performing surface enhanced Raman spectroscopy (SERS) is disclosed. The method of includes the steps of: providing an integrated radiation source/amplifying structure; providing an analyte adjacent the SERS-active structure; generating excitation radiation from the radiation source; amplifying the excitation radiation within the resonant cavity, the amplified radiation impinging on at least a portion of the SERS-active structure and the analyte so as to effect Raman scattering of the amplified radiation by the analyte; and detecting the Raman scattered radiation.

The present invention also includes integrated excitation radiation sources and radiation amplifying structures for use in hyper-SERS, systems employing such structures, and methods for performing hyper-SERS.

These features, advantages, and alternative aspects of the present invention will be apparent to those skilled in the art from a consideration of the following detailed description taken in combination with the accompanying, drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes integrated excitation radiation sources and radiation amplifying structures for use in surface enhanced Raman spectroscopy, systems employing such structures, and methods for performing surface-enhanced Raman spectroscopy (SERS) and hyper-SERS.

Structures having resonant cavities therein, such as Fabry-Perot resonant cavities or resonant defect cavities in photonic crystals, can be used to amplify the intensity of radiation impinging on the article within the cavity. A SERS sample to be analyzed (referred to herein as an "analyte") may be positioned within one of these cavities to subject it to the amplified radiation therein. Fabry-Perot resonant cavities and resonant defect cavities in photonic crystals may amplify radiation of specific frequencies, which are at least partly determined by the physical dimensions of the resonant cavity. Radiation amplifying structures including such resonant cavities may be integrated with an excitation radiation source, such as a vertical cavity surface emitting laser (VCSEL), to decrease the size of a conventional SERS system and to improve the spectroscopic capabilities of the system.

Figure 1A:
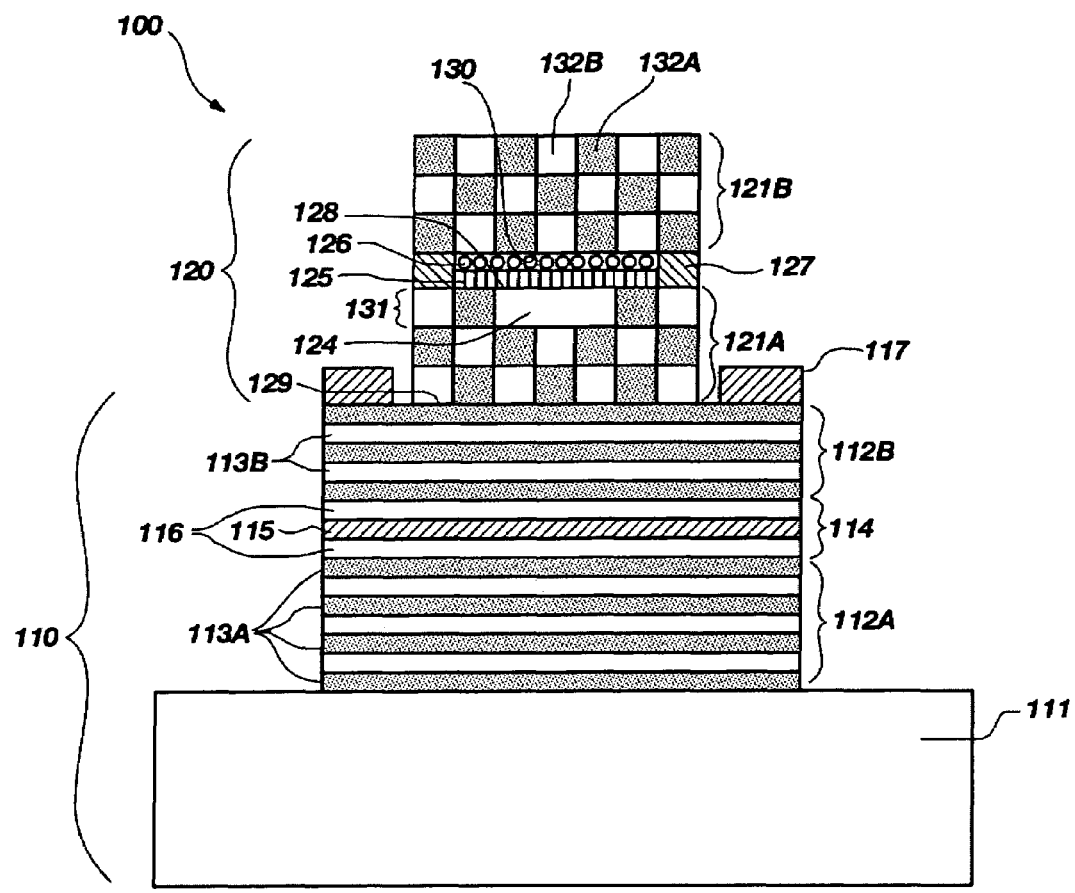
FIG. 1A is a sectional view of an exemplary integrated light source/amplifying structure.

An exemplary integrated radiation source/amplifying structure 100 is shown in FIG. 1A. The structure 100 includes an excitation radiation source 110 and a radiation amplifying structure 120, which may embody various different radiation amplifying structures, examples of which are disclosed herein.

The structure 100 includes a VCSEL excitation radiation source 110. Various embodiments of VCSEL structures and methods of manufacturing VCSEL's are known in the art and may be used in the integrated radiation source/amplifying structure 100. An exemplary embodiment of a VCSEL 110 that may be used with the structure 100 includes a substrate 111, a first Bragg mirror (i.e., a distributed Bragg reflector (DBR)) 112A, a second Bragg mirror 112B, an active region 114, and at least one electrical contact 117.

Bragg mirrors are highly reflective structures and may have a reflectivity as high as about 99.99%. Bragg mirrors include a multilayer stack of alternating layers of high- and low-refractive index materials, shown in FIG. 1B, for example, as low-index layers 113A and high-index layers 113B. Reflectivity generally increases with the number of alternating layers. For simplicity in illustration, first Bragg mirror 112A is shown having four low-index layers 113A and three high-index layers 113B, and the second Bragg mirror 112B is shown having three low-index layers 113A and two high-index layers 113B. However, the Bragg mirrors may comprise up to about 60 pairs of high-index and low-index layers. In addition, either the first Bragg mirror 112A or the second Bragg mirror 112B may comprise more layers, less layers, or an equal number of layers than the other Bragg mirror.

The optical thicknesses of the layers 113A and 113B may be selected to be approximately one-fourth the wavelength of the lasing light (i.e., the excitation radiation) generated in the active region 114 of the VCSEL 110 (i.e., having a thickness of λ/4n, where λ is the wavelength of the incident light and n is the refractive index of the material).

Incident excitation radiation for a SERS system is typically within (although not limited to) the visible range of the electromagnetic spectrum, having a wavelength of between about 350 and about 1000 nanometers. Therefore, if the lasing light were to have a wavelength of 800 nanometers, the optical thickness of the low-index layers 113A and the high-index layers 113B may be approximately 200 nanometers.

The low-index layers 113A and the high-index layers 113B of the Bragg mirrors may be formed from any suitable semiconductor material. As an example, the layers may be formed from aluminum gallium arsenide having alternating concentrations of aluminum. Other examples of suitable material combinations for low-index layers 113A and high-index layers 113B include, but are not limited to: Si and $SiO_2$; GaN and GaAlN; and GaInAsP and InP. Many such suitable material pairs are known in the art and are intended to be included within the scope of the invention. In addition, the first Bragg mirror 112A and the second Bragg mirror 112B are alternatively doped with either a p-type dopant or an n-type dopant. As an example, the first Bragg mirror 112A may be n-type doped and the second Bragg mirror 112B may be p-type doped.

The active region 114, the region where the lasing light is generated, may include a quantum well or active layer 115 and cladding layers 116. Additional quantum wells and cladding layers may be provided to improve the performance of the active area. The active layer 115 may be formed from doped gallium arsenide and the cladding layers 116 may be formed from undoped gallium arsenide. Each of the active layer 115 and the cladding layers 116 may be from about 50 angstroms to about 500 angstroms thick. It is not necessary that the thicknesses of the layers be equal; however, the total thickness of the active region 114, including active layer 115 and cladding layers 116, may be approximately equal to one wavelength of the lasing light generated in the active layer 115 or multiples thereof, or multiples of half wavelength or other fractions.

At least one electrical contact 117 may be formed on the second Bragg mirror 112B from any suitable conductive material, including but not limited to gold, silver, copper, aluminum, any other suitable metal or metal alloy, or a heavily doped semiconductor material. The electrical contact may have a thickness between about 0.1 micron and about 1 micron or thicker.

Substrate 111 may be formed from a semiconductor material, such as gallium arsenide, indium phosphide or silicon. All features of the VCSEL 110, including the first Bragg mirror 112A, the active region 114, the second Bragg mirror 112B, and the electrical contact 117 may be formed using conventional microelectronic fabrication techniques on the substrate 111. Examples of techniques for depositing material layers include but are not limited to molecular beam epitaxy (MBE), atomic layer deposition (ALD), chemical vapor deposition (CVD), physical vapor deposition (PVD), sputter deposition and other known microelectronic layer deposition techniques. Photolithography may be used to form structures in layers, such as a cavity in a cavity layer. Examples of techniques that can be used for selectively removing portions of the layers include, but are not limited to, wet etching, dry etching, plasma etching, and other known microelectronic etching techniques. These techniques are known in the art and will not be further described herein.

To generate the lasing light in the VCSEL 110, a voltage may be applied between the electrical contact 117 and the doped substrate 111. Current passing through the active region 115 of the VCSEL will excite electrons and holes in the active area to an excited state. Photons (i.e., light) may be emitted when the electrons and holes recombine and return to a lower energy state. These emitted photons may reflect back and forth between the first Bragg mirror 112A and the second Bragg mirror 112B. If the distance separating the first Bragg mirror 112A and the second Bragg mirror 112B is an integer multiple of one half the wavelength of the lasing light, the reflected light may interfere constructively, causing amplification thereof. Some of the amplified lasing light will be emitted from the top surface of the VCSEL 110, where it will then interact with the radiation amplifying structure 120, which may be positioned adjacent the VCSEL 110.

With continued reference to FIG. 1A, the radiation amplifying structure 120 may be disposed adjacent to the upper surface of the VCSEL 110. In the radiation amplifying structure such as a resonant optical cavity, the amplification is defined as the ratio of the radiation amplitude inside the structure to the radiation amplitude outside the structure as greater than unity. The radiation amplifying structure 120 includes a bottom layer 121A and a top layer 121B, which may be separated by spacers 127 and a SERS-active structure 125. The bottom layer 121A may include an upper surface 128 and a lower surface 129. The top layer 121B may include a face 130 opposing the upper surface 128 of the bottom layer 121A. An analyte 126 may be disposed adjacent the SERS-active structure 125 during operation of the device.

The top layer 121B, the SERS-active structure 125, and the bottom layer 121A may be formed separately and attached and secured together or merely held in place by gravity or by weak Van der Waals forces, or may be formed together layer-by-layer.

As shown in FIG. 1A, a predetermined amount of standoff between the bottom layer 121A and the top layer 121B may be provided by spacers 127. As an example, the spacers 127 may include epoxy pillars that bond the opposing surfaces of the bottom layer 121A and the top layer 121B together. Alternatively, the spacers 127 may include bricks of solder stenciled or screened onto metallic pads (not shown) on the opposing surfaces of the bottom layer 121A and the top layer 121B and the assembly of the bottom layer 121A and the top layer 121B may then be heated to re-flow the solder thereby bonding the opposing surfaces together. The spacers 127 alternatively may include preformed glass pillars that are bonded to or formed on at least one of the opposing surfaces of the bottom layer 121A and the top layer 121B at the corners thereof. If spacers 127 are bonded to the top and bottom layers, an adhesive such as, for example, an epoxy or any other suitable adhesive may be used to bond the materials together. The spacers 127 may also be formed from a semiconductor material, such as silicon, directly on the upper surface 128 of the bottom layer 121A.

Again referring to FIG. 1A, the SERS-active structure 125 disposed between the bottom layer 121A and the top layer 121B is used to enhance the Raman signal produced by photons of the lasing light that are inelastically scattered by the analyte 126 during analysis. The SERS-active structure 125 may be used to effect electromagnetic enhancement of the Raman signal, chemical enhancement of the Raman signal, or both. As used herein, the term "SERS-active structure" means any structure configured and formed of a material that may produce enhancement of the Raman signal. The representative SERS-active structure 125 illustrated in FIG. 1A comprises an array of vertical, substantially cylindrical columns having a diameter, preferably less than about 20 nanometers, and in some cases greater than 1 nm in its smallest dimensions. Alternative SERS-active structures include, but are not limited to, arbitrarily and selectively arranged particles, dots, columns, rods, columns, pyramids, or any other shape or structure that is capable of enhancing the Raman signal produced by atoms or molecules adsorbed thereon or positioned near thereto, including a simple roughened metal surface.

Exemplary materials for the SERS-active structure 125 include, but are not limited to, gold, silver, copper, aluminum, chromium, lithium, sodium, potassium, or another suitable material capable of enhancing the Raman signal produced by atoms or molecules adsorbed thereon or positioned near thereto.

The SERS-active structure 125 may be chemically bonded to the upper surface 128 of the bottom layer 121A or merely disposed thereon and weakly bonded thereto, if bonded at all.

Although the materials that form the SERS-active structure 125 typically are not transparent to the typical wavelengths of light used in Raman spectroscopy (about 350 nm to about 1000 nm), the SERS-active structure may be formed with apertures or spaces therethrough (such as the spaces between the columns) to allow the excitation radiation generated by the VCSEL 110 to pass through the SERS-active structure 125.

The bottom layer 121A and the top layer 121B may include photonic crystals. Photonic crystals are formed by dispersing a material of one refractive index periodically within a matrix having a different refractive index. A one-dimensional photonic crystal is a three-dimensional structure that exhibits periodicity in refractive index in only one dimension. Bragg mirrors are an example of a one-dimensional photonic crystal. The alternating thin layers have different refractive indices. The combination of several thin layers forms a three-dimensional structure that exhibits periodicity in refractive index in only the direction orthogonal to the planes of the thin layers. No periodicity is exhibited in either of the two dimensions contained within the plane of the layers.

A two-dimensional photonic crystal can be formed by periodically dispersing rods or columns of a material of one refractive index within a matrix having a different refractive index. Two-dimensional photonic crystals exhibit periodicity in only two dimensions, i.e., the directions perpendicular to the length of the rods or columns, but no periodicity is exhibited in the direction parallel to the length of the columns.

Finally, a three-dimensional photonic crystal can be formed by periodically dispersing small spheres or other spatially confined areas of a first material having a first refractive index within a matrix of a second material having a second, different, refractive index. Three-dimensional photonic crystals exhibit periodicity in refractive index in all three dimensions within the crystal.

Figure 10A:
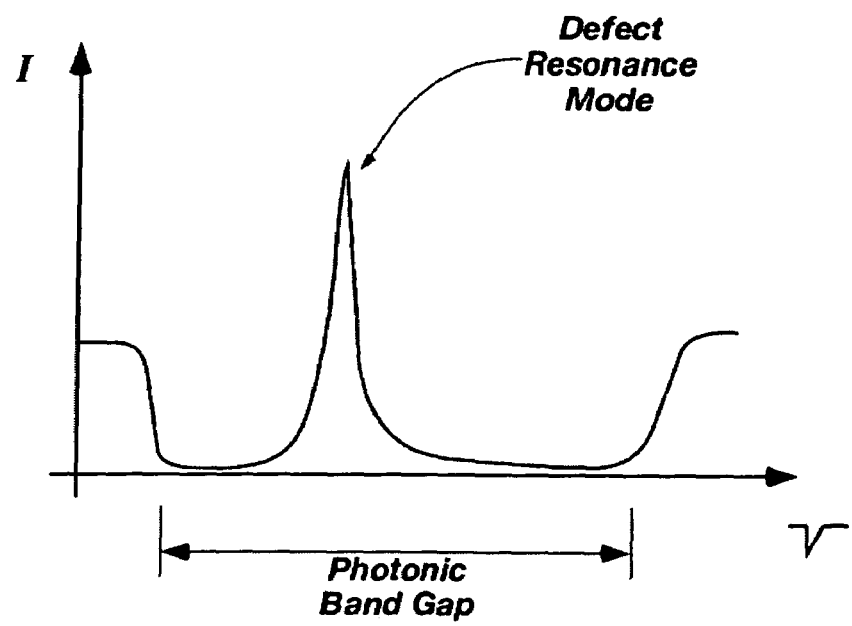
FIG. 10A is an exemplary graph of intensity as a function of frequency within a resonant defect cavity within a photonic crystal device illustrating a photonic band gap and a defect mode associated with the defect cavity within the photonic bandgap.

Photonic crystals may exhibit a photonic bandgap within a range of certain frequencies in the directions exhibiting periodicity in refractive index (see FIG. 10A). In other words, there is a range of frequencies of radiation or light that will not be transmitted through the crystal in the directions exhibiting periodicity in refractive index. This range of frequencies that are not transmitted is known as the photonic bandgap of the photonic crystal. No photonic bandgap is exhibited in directions that do not exhibit periodicity in refractive index.

When the periodicity in refractive index in a photonic crystal is interrupted, perhaps by a defect or a missing layer in a Bragg mirror, certain defect modes may be generated. Defect modes allow certain frequencies of light within the band gap to be partially transmitted through the crystal and enter into the defect area where the photons of the radiation are at least partially trapped or confined. As more photons enter the defect and become trapped or confined, the light may be amplified. The frequencies associated with the defect modes are, at least partially, a function of the dimensions of the defect.

The bottom layer 121A and the top layer 121B may include three-dimensional photonic crystals formed from stacked, offset two-dimensional photonic crystal layers 131. The two-dimensional photonic crystal layers 131 may be formed by periodically dispersing columns or rods 132A of a first material periodically within a matrix 132B of a second material. Examples of suitable materials for the columns or rods 132A and the matrix 132B in which they are disposed include, but are not limited to: GaAs and AlGaAs, AlGaAs columns within an AlGaAs matrix having different atomic percents of Al and Ga, GaN and GaAlN, Si and $SiO_2$, Si and SiN, and GaInAsP and InP. In practice, virtually any two materials that have different refractive indices can be used. Alternatively, the matrix 132B may be formed of a semiconductive material and the rods 132A may simply comprise air gaps formed by etching rod-shaped apertures through the semiconductive matrix 132B.

Each of the bottom layer 121A and the top layer 121B are shown having three two-dimensional photonic crystal layers 131. The bottom layer 121A and the top layer 121B alternatively may include as many as 60 two-dimensional photonic crystal layers 131, which may be formed in an offset manner on top of one another, such that, for example, the rods 132A of one layer 131 are disposed above an area of matrix 132B in the layer 131 directly below.

Figure 1B:
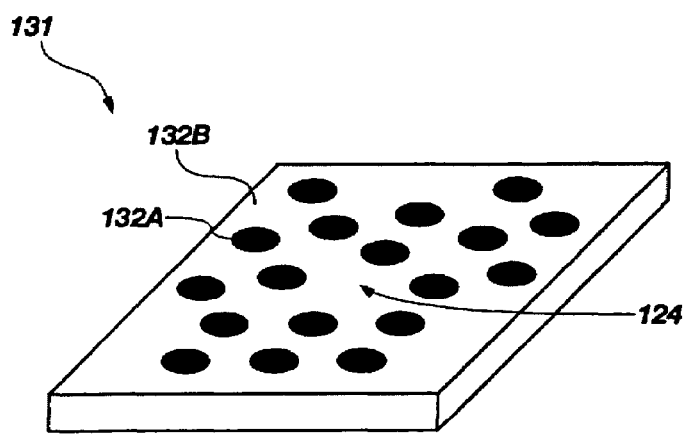
FIG. 1B is a perspective view of a two-dimensional photonic crystal depicted in FIG. 1A.

Referring to FIGS. 1A and 1B, one rod 122 in the center of the top two-dimensional photonic crystal layer 131 of bottom layer 121A is missing, creating a resonant defect cavity 124. Alternatively, the defect could be formed as an air gap or a spatially confined area of a different material such as glass or epoxy.

In this configuration, the radiation amplifying structure 120 may exhibit a photonic band gap for light passing vertically through the structure, such as the excitation radiation emitted from the top surface of the VCSEL 110, as shown in FIG. 1A. The radiation amplifying structure 120 may exhibit a defect mode at a specific wavelength within the photonic band gap associated with the resonant defect cavity 124.

An analyte 126 may be provided adjacent the SERS-active structure 125 in the vicinity of the resonant defect cavity 124 by diffusion of the analyte 126 through small openings provided between spacers 127 on the lateral sides of the radiation amplifying structure 120.

The excitation radiation emitted from the VCSEL 110 may be amplified in the vicinity of the resonant defect cavity 124 when the frequency of the excitation radiation corresponds to a defect mode associated with the resonant defect cavity 124. This amplified excitation radiation will impinge on both the SERS-active structure 125 and the analyte 126 disposed adjacent the SERS-active structure near (or within) the resonant defect cavity 124. The irradiation of the SERS-active structure 125 by the amplified radiation produces a surface enhancement effect therein (i.e., chemical, electromagnetic, or both). In other words, irradiation of the SERS-active structure 125 by the amplified excitation radiation may produce a strong electromagnetic field near the SERS-active structure 125. The analyte 126 adjacent the portion of the SERS-active structure 125 that is being irradiated by the amplified radiation, in turn, experiences this very strong electromagnetic field. At least a portion of the amplified radiation may impinge on the analyte 126 and may be inelastically scattered as Stokes or anti-Stokes radiation (or both) thereby, to produce Raman scattered photons. The electromagnetic field enhances the intensity of the signal produced by Raman photons scattered by the analyte 126. Because the intensity of the Raman photons scattered by the analyte 126 is, in part, proportional to the square of the electromagnetic field experienced by the analyte, the enhancement effect from the SERS-active structure may increase the intensity of the signal of the Raman scattered photons by as much as $10^{14}$.

The present invention also includes integrated excitation radiation sources and radiation amplifying structures for use in hyper-SERS, systems employing such structures, and methods for performing hyper-SERS. Hyper-SERS includes SERS radiation that radiates at double the frequency or half the wavelength of the excitation. This allows the detection to be in the visible light spectrum and also far away from the pumping radiation wavelength. In other words, with hyper-SERS, the surface enhanced Raman radiation can have a wavelength roughly half the impinging, excitation or pumping wavelength that can be observed, thus allowing the detection of the SERS radiation in the visible spectrum. For example, if the pumping radiation is in the infrared spectrum (e.g., about 800 nm range), the SERS radiation will be roughly at 400 nm. This shorter detection wavelength makes possible very sensitive detectors that can be used at room temperature. The integrated excitation radiation sources, radiation amplifying structures, systems and methods described herein can be used to perform hyper-SERS.

Figure 2A:
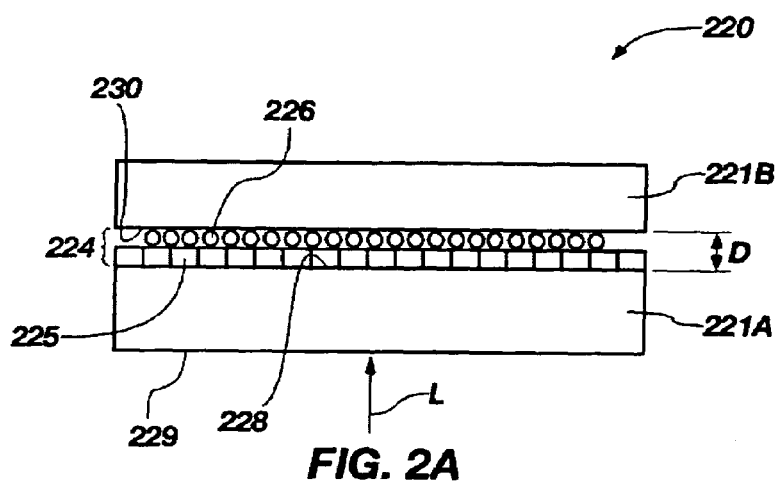
FIG. 2A is a sectional view of an exemplary radiation amplifying structure that may be used in the integrated light source/amplifying structure of FIGS. 1A and 1B.

Many other embodiments of radiation amplifying structures may alternatively be used with the VCSEL 110 of the integrated radiation source/amplifying structure 100 of FIGS. 1A and 1B. For example, an exemplary radiation amplifying structure 220 is shown in FIG. 2A that includes a standoff or resonant cavity 224 separating a bottom layer 221A and a top layer 221B. The bottom layer 221B has an upper surface 228 and a lower surface 229 that are generally parallel to each other. Top layer 221B has a face 230 opposing the upper surface 228 of the bottom layer 221A and is separated therefrom by a distance D. The volume or space between the bottom layer 221A and the top layer 221B defines the standoff or resonant cavity 224. The distance D may be as small as about a monolayer of the analyte 226 being analyzed or more.

The bottom layer 221A and the top layer 221B should be at least partially transparent to the frequency of the excitation radiation generated by the VCSEL 110 that is to be used for spectroscopic analysis. The thickness of the bottom layer 221A and the top layer 221B may be between about 0.1 microns and about 6 microns or more. The bottom layer 221A and the top layer 221B may be formed from a variety of different materials. Exemplary materials for the bottom layer 221A and the top layer 221B include diamond, silicon nitride, silicon dioxide, or any other suitable material. The length and width of the bottom layer 221A and the top layer 221B are not critical, but may be sized to allow the structure to be handled manually, for example, by using tweezers or any other suitable micromanipulator device.

A SERS-active structure 225 is provided between the bottom layer 221A and the top layer 221B within the standoff or resonant cavity 224. The top layer 221B, the SERS-active structure 225, and the bottom layer 221A may be formed separately and attached or secured together or merely held in place by gravity or by weak Van der Waals forces, or may be formed together layer-by-layer.

Figure 2B:
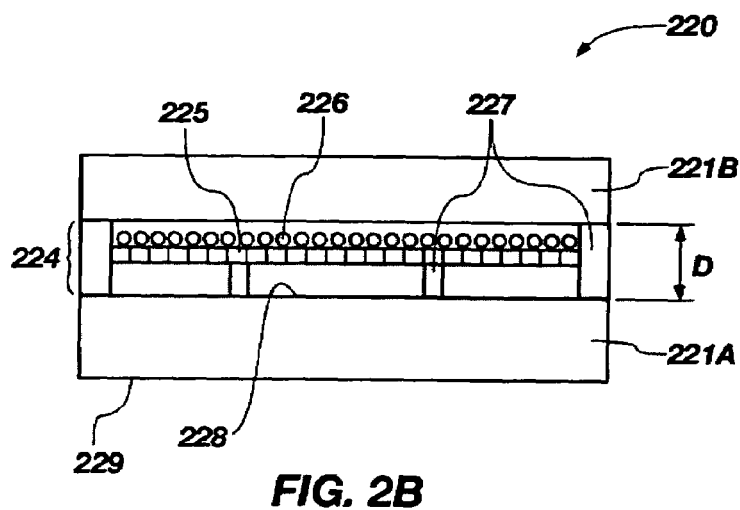
FIG. 2B is a sectional view of an exemplary radiation amplifying structure that may be used in the integrated light source/amplifying structure of FIGS. 1A and 1B that includes spacers.
Figure 2C:
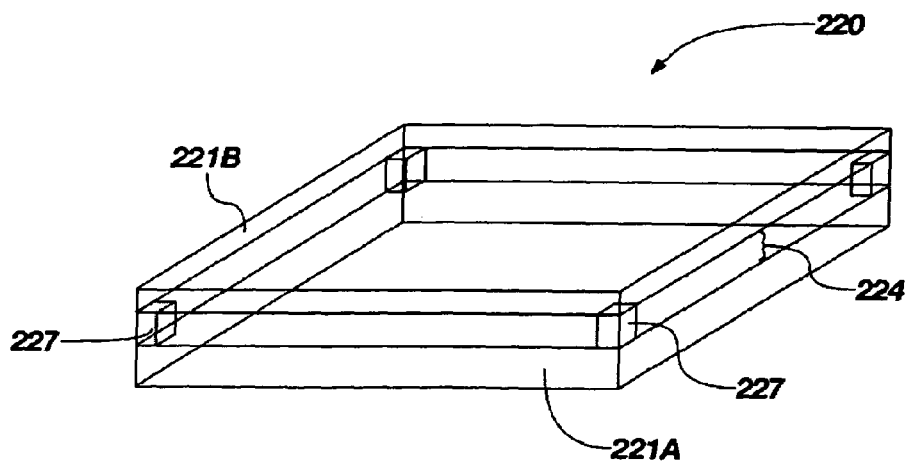
FIG. 2C is a perspective view of the exemplary radiation amplifying structure of FIG. 2B.

As shown in FIG. 2B, a predetermined amount of standoff between the bottom layer 221A and the top layer 221B may be provided using spacers 227. As shown in FIG. 2C, a plurality of spacers 227 may be used, one spacer element being located at each of the corners of the bottom layer 221A and the top layer 221B. The spacers 227 may be identical in all important aspects to the spacers 127 discussed previously in relation to the light amplifying structure 120 (FIG. 1A).

Again referring to FIG. 2A, the SERS-active structure 225 disposed within the cavity 224 enhances the number of photons that are inelastically scattered by the analyte 226 during analysis (i.e., enhances the Raman signal), and may be similar to the SERS-active structure 125 discussed previously in relation to the light amplifying structure 120 (FIG. 1B). However, the representative SERS-active structure 225 illustrated in FIGS. 2A–2B comprises a mesh or screen formed from metallic rods or wires having a diameter preferably less than about 20 nanometers. Referring to FIG. 2B, the SERS-active structure 225 may be positioned at any position within the cavity 224 using spacers 227 to support the SERS-active structure 225 vertically within the resonant cavity 224.

The operation of the radiation amplifying structure 200 is described with reference to FIG. 2A. The cavity 224 functions as Fabry-Perot resonating cavity. A simple Fabry-Perot resonator includes two parallel, flat, material layers. The bottom layer 221A and top layer 221B of the light amplifying structure 220 function as the material layers of a Fabry-Perot resonator. A resonant cavity is formed by at least a portion of the cavity 224 between the bottom layer 221A and the top layer 221B. The materials forming the bottom layer 221A and the top layer 221B have a refractive index different from that of the cavity 224. When excitation radiation emitted from the VCSEL 110 (FIGS. 1A and 1B) impinges on the lower surface 229 of the bottom layer 221A in the direction illustrated by direction arrow L in FIG. 2A, at least some of the radiation will pass through the bottom layer 221A into the resonant cavity 224. The change or difference in refractive index at the interfaces between the bottom layer 221A and the cavity 224, and between the top layer 221B and the cavity 224, may cause at least some of the excitation radiation to be reflected internally inside the cavity 224 rather than being transmitted through the top layer 221B.

Figure 10B:
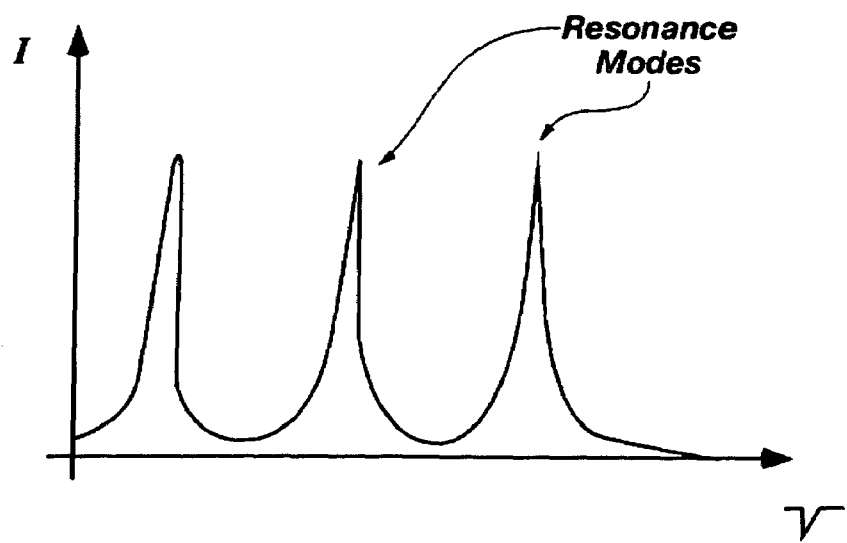
FIG. 10B is an exemplary graph of intensity as a function of frequency within a resonant cavity of a Fabry-Perot resonating device illustrating resonance modes.

When the distance D separating the bottom layer 221A and the top layer 221B is equal to an integer number of half wavelengths of the excitation radiation, the internally reflected radiation may interfere constructively, causing amplification of the intensity and power of the radiation inside the cavity 224. For a Fabry-Perot resonant cavity having a distance D, a graph of intensity of radiation within the resonant cavity as a function of the frequency that the incident excitation radiation produces may have a series of peaks corresponding to the resonance modes of the cavity, similar to that shown by the graph in FIG. 10B. The peaks correspond to wavelengths that satisfy the equation $\lambda=2D/n$, where $\lambda$ is the wavelength of the incident radiation and n is an integer.

Therefore, the distance D must be selected based upon the wavelength of the excitation radiation emitted by the VCSEL 110 (FIGS. 1A and 1B). For example, if the excitation radiation is to have a wavelength of 800 nanometers, then the distance D may be an integer multiple of 400 nanometers. Therefore D could be 800, 1200 nm, 1600 nm, 2000 nm, 8000 nm, etc.

The intensity of the excitation radiation may be amplified within the resonant cavity 224 by a factor of about 1000. Therefore, as an example, if the power of the excitation radiation is 1 mW, the power of the amplified radiation resonating within the cavity 224 may be about 1 W.

When the distance D is not equal to an integer number of half wavelengths of the excitation radiation, the internally reflected light may interfere destructively, causing the intensity of the light inside the cavity 224 to be diminished, which may render the radiation amplifying structure ineffective for exciting the analyte for SERS.

A reflective coating may be provided on the upper surface 228 of the bottom layer 221A and the opposing face 230 of the top layer 221B. Reflective coatings may be made from diamond or any other material that will at least partially reflect the incident radiation. The reflective coatings may cause more of the radiation to reflect internally inside the cavity, instead of being transmitted through the dielectric material layers, thereby further increasing the intensity of the resonating radiation inside the cavity.

Figure 3:
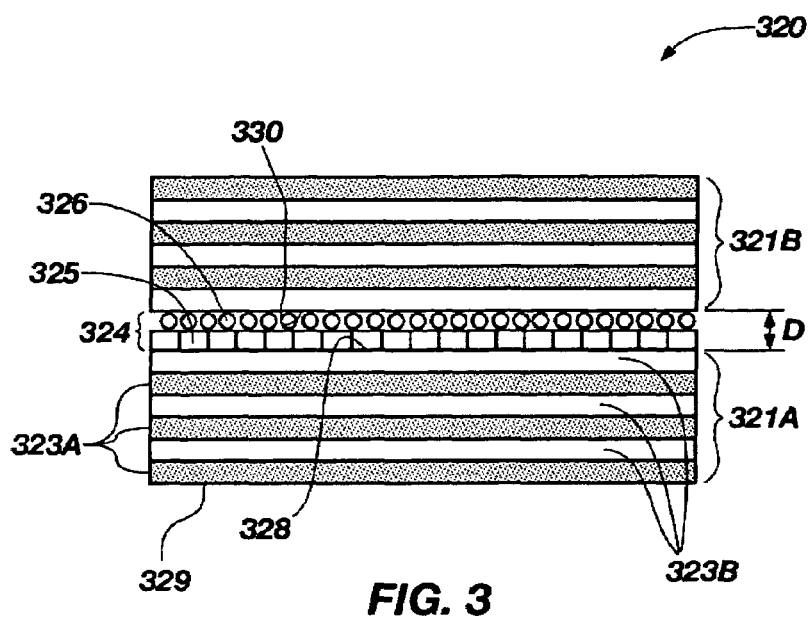
FIG. 3 is a sectional view of an exemplary radiation amplifying structure that may be used in the integrated light source/amplifying structure of FIGS. 1A and 1B that includes Bragg mirrors.

Another exemplary embodiment of a radiation amplifying structure 320 that may be integrated with a radiation source, as shown in FIGS. 1A and 1B, is illustrated in FIG. 3. The radiation amplifying structure 320 includes a standoff or resonant cavity 324 separating a bottom layer 321A and a top layer 321B. The bottom layer 321A has an upper surface 328 and a lower surface 329 that are generally parallel to each other, but can also be confocal and other non parallel mirrors for stable or unstable resonant cavities. Top layer 321B has a face 330 opposing the upper surface 328 of the bottom layer 321A and is separated therefrom by a distance D. At least a portion of the volume or space between the bottom layer 321A and the top layer 321B defines the standoff or resonant cavity 324. The distance D may be as small as about a monolayer of the analyte 326 being analyzed or greater.

The bottom layer 321A and the top layer 321B of the radiation amplifying structure 320 include Bragg mirrors, which may be identical in all respects to the first Bragg mirror 112A and the second Bragg mirror 112B described with reference to and shown in FIG. 1B. However, the alternating layers of the first Bragg mirror 321A and the second Bragg mirror 321B need not be doped since a voltage or current will not be applied across the light amplifying structure 320. The bottom layer 321A and the top layer 321B may include alternating layers 323A and 323B of low refractive index and high refractive index, respectively, such as, for example, aluminum gallium arsenide having alternating concentrations of aluminum. Other examples of suitable material combinations for low-index layers 323A and high-index layers 323B are well known and may include, but are not limited to: Si and $SiO_2$; GaN and GaAlN; and GaInAsP and InP. Many such suitable material pairs are known in the art and are intended to be included within the scope of the invention.

The radiation amplifying structure 320 may function as a Fabry-Perot resonating device in the same manner discussed previously in relation to the radiation amplifying structure 220 of FIG. 2A. In addition, Bragg mirrors can function as one-dimensional photonic crystals. A photonic band gap may exist in the direction orthogonal to the planes of the thin layers. The cavity 324 between the bottom layer 321A and the top layer 321B provides a discontinuity or defect in the periodicity in refractive index in the direction orthogonal to the plane of the layers. At least one defect mode within the band gap may be generated as a result of the discontinuity of the periodicity in refractive index generated by the resonant cavity 324. The frequency of radiation associated with this defect mode may be amplified within the interior of the cavity 324, and may be used as the excitation radiation in a SERS system. Thus, the cavity 324 may operate as a resonant defect cavity within a photonic crystal, in addition to operating as a Fabry-Perot resonating cavity.

The exemplary SERS-active structure 325 shown in FIG. 3 may comprise an array of metallic nanospheres having a diameter less than about 20 nanometers.

Figure 4A:
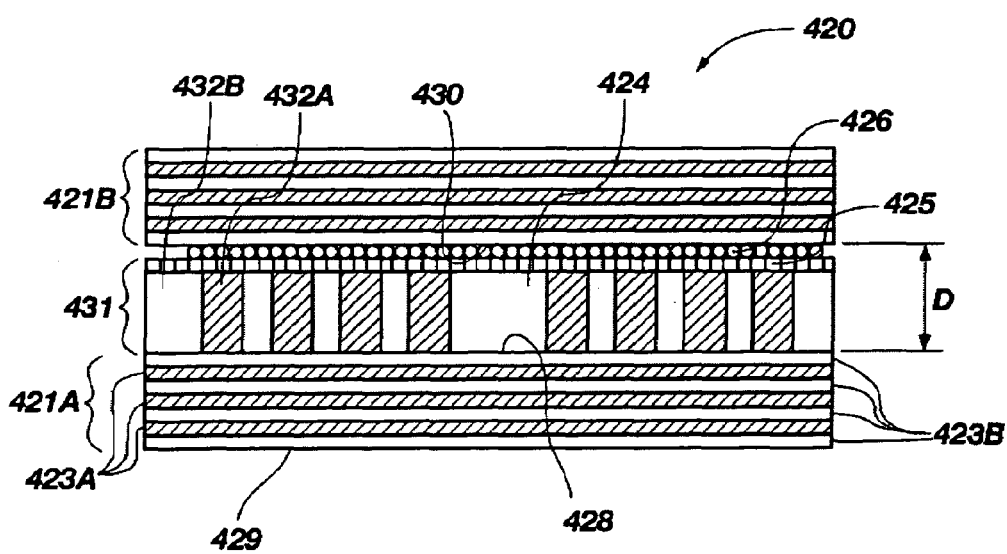
FIG. 4A is a sectional view of an exemplary radiation amplifying structure that may be used in the integrated light source/amplifying structure of FIGS. 1A and 1B that includes Bragg mirrors and a cavity layer between the mirrors.

Another exemplary embodiment of a radiation amplifying structure 420 that may be integrated with a radiation source, as shown in FIGS. 1A and 1B, is illustrated in FIG. 4. The radiation amplifying structure 420 includes a bottom layer 421A and a top layer 421B. The bottom layer 421A has an upper surface 428 and a lower surface 429 that are generally parallel to each other. Top layer 421B has a face 430 opposing the upper surface 428 of the bottom layer 421A and is separated therefrom by a distance D. A cavity layer 431 and a SERS-active structure 425 may be provided between the bottom layer 421A and the top layer 421B. An analyte 426 may be positioned adjacent at least a portion of the SERS-active structure 425. Although not shown in FIG. 4A, spacers identical to spacers 227 (FIG. 2B) may be used to provide a predetermined amount of standoff (thereby increasing the distance D) between the opposing surfaces of the cavity layer 431 and the top layer 421B. The cavity layer 431 may include a two-dimensional photonic crystal that has a resonant defect cavity 424. However, it is not necessary for the cavity layer 431 to be formed as a two-dimensional photonic crystal. Any layer containing a suitable cavity 424 may be used to form the cavity layer 431. For example, a silica microsphere may be embedded in a layer comprising a matrix of material, such as silicon, having a different refractive index than that of the silica.

With continuing reference to FIG. 4A, the bottom layer 421A and the top layer 421B may include Bragg mirrors similar to those discussed previously in relation to the light-amplifying structure 320 of FIG. 3 and the VCSEL 110 of FIG. 1B, having alternating layers of low-index material 423A and high-index material 423B.

Figure 4B:
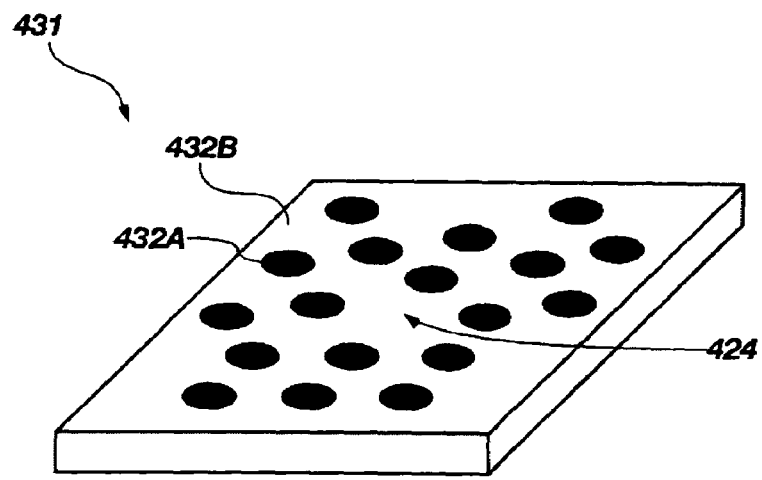
FIG. 4B is a perspective view of the cavity layer depicted in FIG. 4A.

Referring to FIGS. 4A and 4B, the cavity layer 431 may comprise a two-dimensional photonic crystal exhibiting periodicity in refractive index in all directions parallel to the plane of the cavity layer. The two-dimensional photonic crystal of the cavity layer 431 may include columns or rods 432A of a first material periodically dispersed within a matrix 432B of a second material. However, one rod in the center of the cavity layer 431 is missing, creating a resonant defect cavity 424.

Examples of suitable materials for the columns or rods 432A and the matrix 432B in which they are disposed include, but are not limited to: GaAs and AlGaAs; AlGaAs columns within an AlGaAs matrix having different atomic percents of Al and Ga than the columns; GaN and GaAlN; Si and $SiO_2$; Si and SiN; and GaInAsP and InP. In practice, virtually any two materials that have different refractive indices may be used.

In this configuration, the cavity layer 431 may exhibit a photonic band gap for light passing through the layer in any direction parallel to the plane of the layer, and may exhibit a defect mode associated with the defect of cavity 424 at a frequency within the photonic band gap (FIG. 10A).

The resonant cavity 424 of the radiation amplifying structure 420 of FIG. 4A operates in a similar fashion to the radiation amplifying structure 320 of FIG. 3, and may amplify the excitation radiation emitted from the VCSEL 110 (FIG. 1) in two ways. First, the structure 420 may operate as a Fabry-Perot resonant cavity when the distance separating the lower layer 421A and the top layer 421B is an integer multiple of one half of the wavelength of the excitation radiation emitted from the VCSEL 110, as discussed previously in relation to the radiation amplifying structure 220 of FIG. 2. Alternatively, the excitation radiation may be amplified within the resonant cavity 424 when the wavelength of the radiation corresponds to a defect mode associated with the resonant cavity 424 between the Bragg mirrors of the bottom layer 421A and the top layer 421B, as discussed previously in relation to the radiation amplifying structure 300 of FIG. 3.

Cavity layer 431 is a two-dimensional photonic crystal and may exhibit a photonic bandgap and defect modes in any direction parallel to the plane of the cavity layer 431. Radiation having a frequency within the photonic band gap of cavity layer 431 may not be transmitted through the layer in any direction parallel to the plane of the cavity. Therefore, the wavelength of the excitation radiation emitted from the VCSEL 110 may be selected to be within a photonic band gap of the two-dimensional photonic crystal that forms the cavity layer 431 (or the cavity layer 431 may be designed to exhibit a photonic bandgap over the range of wavelengths of the desired excitation radiation). Thus, cavity layer 431 may confine the excitation radiation within the area proximate the cavity 424, the SERS-active structure 425, and the analyte 426, by preventing the excitation radiation from propagating in any direction parallel to the plane of the cavity layer 431. In this manner, the efficiency of the radiation amplifying structure 420 may be increased relative to the radiation amplifying structures 220 (FIGS. 2A–2C) and 320 (FIG. 3).

Figure 5:
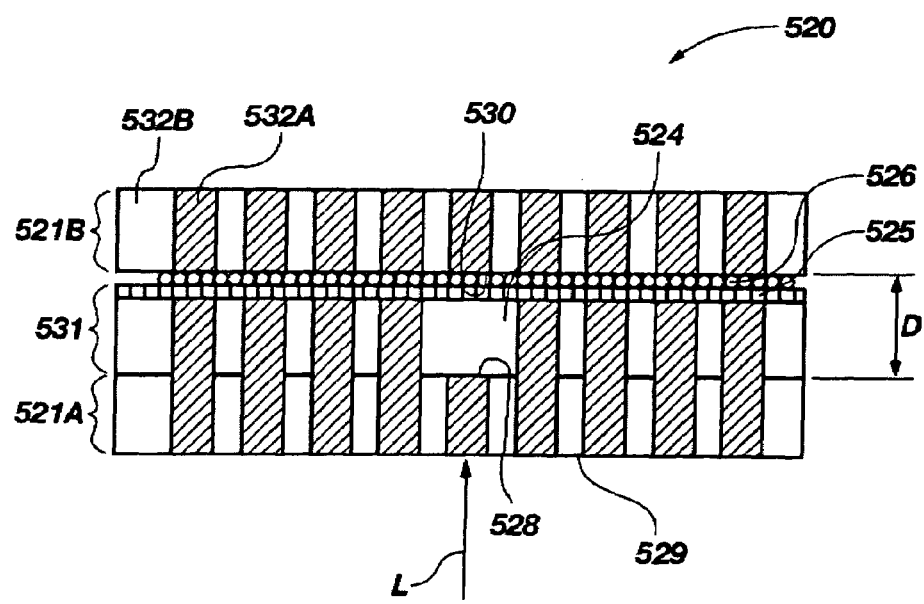
FIG. 5 is a sectional view of an exemplary radiation amplifying structure that may be used in the integrated light source/amplifying structure of FIGS. 1A and 1B that includes multiple two-dimensional photonic crystals.

Another exemplary embodiment of a radiation amplifying structure 520 that may be integrated with a radiation source, as shown in FIGS. 1A and 1B, is illustrated in FIG. 5. The structure 520 includes a bottom layer 521A and a top layer 521B that include two-dimensional photonic crystals. The bottom layer 521A has an upper surface 528 and a lower surface 529 that are generally parallel to each other. Top layer 521B has a face 530 opposing the upper surface 528 of the bottom layer 521A and is separated therefrom by a distance D. A cavity layer 531 and a SERS-active structure 525 may, be provided between the bottom layer 521A and the top layer 521B. An analyte 526 may be positioned adjacent at least a portion of the SERS-active structure 525. Although not shown in FIG. 5, spacers identical to spacers 227 (FIG. 2B) may be used to provide a predetermined amount of standoff (thereby increasing the distance D) between the opposing surfaces of the cavity layer 531 and the top layer 521B. The cavity layer 531 may be identical in all respects to the cavity layer 431 of FIGS. 4A and 4B. Optionally, the bottom layer 521A and the cavity layer 531 may be formed as a unitary or monolithic structure and need not be formed from separate layers. As with the aforementioned embodiments, spacers (not shown) identical to spacers 227 of FIG. 2B may be used to provide a predetermined amount of standoff between the opposing surfaces of the cavity layer 531 and the top layer 521B, thereby changing the distance D.

Because the bottom layer 521A, the top layer 521B and the cavity layer 531 each are formed as two-dimensional photonic crystals exhibiting periodicity in refractive index in directions parallel to the plane of the layers, each layer may exhibit a photonic band gap in any direction parallel to the planes of the layers. No photonic bandgap will be exhibited in the direction orthogonal to the planes of the layers because no periodicity in refractive index is exhibited in that direction. The bottom layer 521A and top layer 521B may operate as the material layers of a Fabry-Perot resonating device in the same way described above in reference to the radiation amplifying structure 220 of FIG. 2A. Therefore, excitation radiation emitted from the VCSEL 110 of FIG. 1B that enters the radiation amplifying structure 520 in the direction L shown in FIG. 5 may resonate and be amplified within cavity 524 when the distance D is equal to an integer multiple of one half of the wavelength of the excitation radiation. If the bottom layer 521A, the top layer 521B and the cavity layer 531 are designed to exhibit a photonic bandgap that includes the wavelength or frequency of the excitation radiation, the excitation radiation may be at least partially confined in the area of the resonant cavity 524 and the portion of the analyte 526 adjacent thereto by the photonic crystal layers, thereby increasing the efficiency of the amplification of the excitation radiation within the resonant cavity 524.

Figure 6:
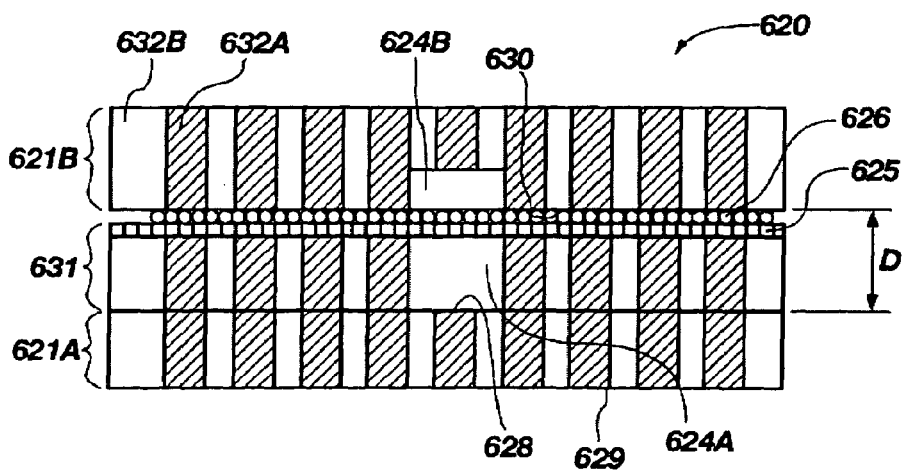
FIG. 6 is a sectional view of an exemplary radiation amplifying structure that may be used in the integrated light source/amplifying structure of FIGS. 1A and 1B that includes a resonant cavity formed by a defect in more than one layer.

Another exemplary embodiment of a radiation amplifying structure 620 that may be integrated with a radiation source, as shown in FIGS. 1A and 1B, is illustrated in FIG. 6. The structure 620 includes a bottom layer 621A and a top layer 621B that include two-dimensional photonic crystals. The bottom layer 621A has an upper surface 628 and a lower surface 629 that are generally parallel to each other. Top layer 621B has a face 630 opposing the upper surface 628 of the bottom layer 621A and is separated therefrom by a distance D. A cavity layer 631 and a SERS-active structure 625 may be provided between the bottom layer 621A and the top layer 621B. An analyte 626 may be positioned adjacent at least a portion of the SERS-active structure 625. Although not shown in FIG. 6, spacers identical to spacers 227 (FIG. 2B) may be used to provide a predetermined amount of standoff (thereby increasing the distance D) between the opposing surfaces of the cavity layer 631 and the top layer 621B. The cavity layer 631 may be identical in all respects to the cavity layer 431 of FIGS. 4A and 4B. Optionally, the bottom layer 621A and the cavity layer 631 may be formed as a unitary or monolithic structure and need not be formed from separate layers. As with the aforementioned embodiments, spacers (not shown) identical to spacers 227 of FIG. 2B may be used to provide a predetermined amount of standoff between the opposing surfaces of the cavity layer 631 and the top layer 621B, thereby changing the distance D.

The SERS-active structure 625 is located at an optimal position inside the resonant cavity 624, which may be collectively defined by the partial cavity 624A of the cavity layer 631, the additional partial cavity 624B of the top layer 621B, and at least a portion of the volume of the standoff between the top layer 621B and the cavity layer 631. For example, the SERS-active structure 625 may be positioned at a location within the cavity 624 where the intensity of the excitation radiation is between about 80% and about 100% of the maximum optical intensity within the cavity. By positioning the SERS-active structure 625 at such a location within the resonant cavity 624, the strength of the signal produced by Raman scattered photons may be increased.

The radiation amplifying structure 620 of FIG. 6 may operate in substantially the same manner as the radiation amplifying structure 520 of FIG. 5, discussed previously herein.

Figure 7A:
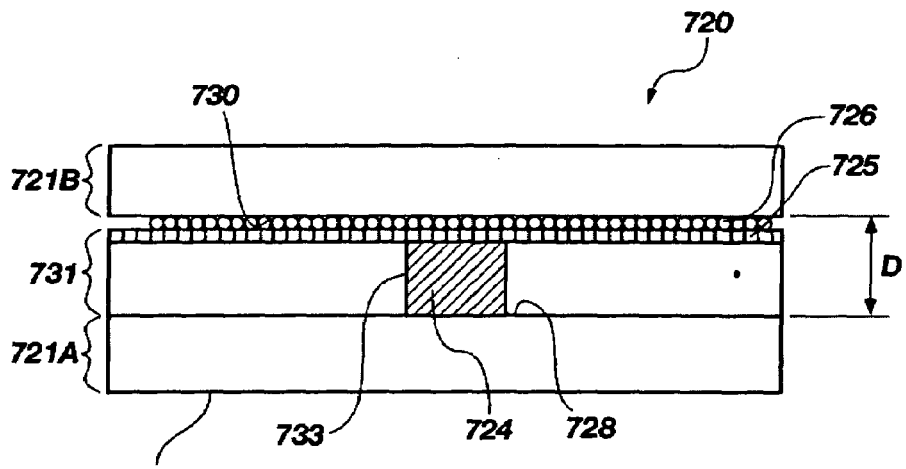
FIG. 7A is a sectional view of an exemplary radiation amplifying structure that may be used in the integrated light source/amplifying structure of FIGS. 1A and 1B that includes a cavity layer.
Figure 7B:
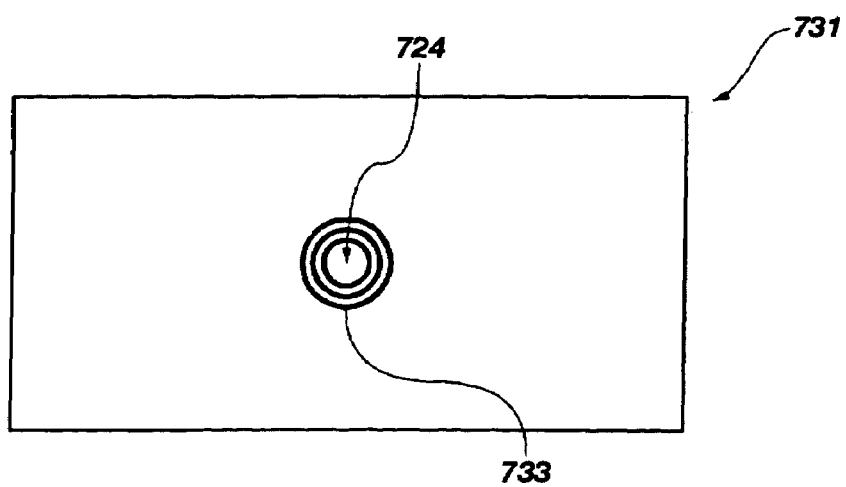
FIG. 7B is a plan view of the cavity layer shown in FIG. 7A depicting a cavity at the center thereof.

Another exemplary embodiment of a radiation amplifying structure 720 that may be integrated with a radiation source, as shown in FIGS. 1A and 1B, is illustrated in FIGS. 7A and 7B. The structure 720 includes a bottom layer 721A and a top layer 721B that include two-dimensional photonic crystals. The bottom layer 721A has an upper surface 728 and a lower surface 729 that are generally parallel to each other. Top layer 721B has a face 730 opposing the upper surface 728 of the bottom layer 721A and is separated therefrom by a distance D. A cavity layer 731 and a SERS-active structure 725 may be provided between the bottom layer 721A and the top layer 721B. An analyte 726 may be positioned adjacent at least a portion of the SERS-active structure 725. Although not shown in FIGS. 7A or 7B, spacers identical to spacers 227 (FIG. 2B) may be used to provide a predetermined amount of standoff (thereby increasing the distance D) between the opposing surfaces of the cavity layer 731 and the top layer 721B. Optionally, the bottom layer 721A and the cavity layer 731 may be formed as a unitary or monolithic structure and need not be formed from separate layers.

However, unlike the three-layer radiation amplifying structures 420, 520, and 620 disclosed in FIGS. 4A, 5, and 6, respectively, photonic crystals are not employed in any of the bottom layer 721A, the top layer 721B, and the cavity layer 731. The bottom layer 721A and the top layer 721B may be formed from a first dielectric material having a first refractive index. The cavity layer 731 may include a resonant cavity 724, which may be formed as a spatially confined area of a second dielectric material or as a void (e.g., a void containing air) having a second refractive index embedded in the first dielectric material. For example, the cavity 724 may be formed as a silica microsphere embedded in the first dielectric material.

An exemplary cavity 724 is illustrated in the plan view of cavity layer 731 in FIG. 7B. The cavity 724 may include a generally cylindrical structure having a surface 733. The surface 733 defines the boundary between the first dielectric material of the cavity layer 731 and the cavity 724, and may comprise multiple pairs of adjacent cylindrical layers of alternating refractive indices to form a cylindrical Bragg mirror, similar to the conventional planar Bragg mirrors described previously in relation to the VCSEL 110 (FIG. 1B) and radiation amplifying structures 320 (FIG. 3) and 420 (FIG. 4), and may include the same materials.

The radiation amplifying structure 720 of FIG. 7A may operate as a Fabry-Perot resonating device as discussed previously in relation to the radiation amplifying structure 220 of FIG. 2. The cavity layer 731 may operate to confine the excitation radiation within the vicinity of the resonant cavity 724 and at least a portion of the SERS-active structure 725 and an analyte 726 disposed adjacent thereto, as discussed previously in relation to the cavity layer 431 of FIG. 4.

All features of the integrated radiation source/amplifying structure 100, including all features of the VCSEL 110 and the radiation amplifying structures 120, 220, 320, 420, 520, 620, and 720 may be formed using conventional microelectronic fabrication techniques on a support substrate such as, for example, a silicon wafer, partial wafer, or a glass substrate. Examples of techniques for depositing material layers include, but are not limited to, molecular beam epitaxy (MBE), atomic layer deposition (ALD), chemical vapor deposition (CVD), physical vapor deposition (PVD), sputter deposition and other known microelectronic layer deposition techniques. Photolithography may also be used to form structures in layers, such as a cavity in a cavity layer. Examples of techniques that can be used for selectively removing portions of the layers include, but are not limited to, wet etching, dry etching, plasma etching, and other known microelectronic etching techniques. These techniques are known in the art and will not be further described herein.

In addition, each of the VCSEL 110 and the radiation amplifying structure of the integrated radiation source/amplifying structure 100 may be formed separately and assembled together, or alternatively, may be formed together, for example, by forming the radiation amplifying structure directly on the VCSEL.

Figure 8:
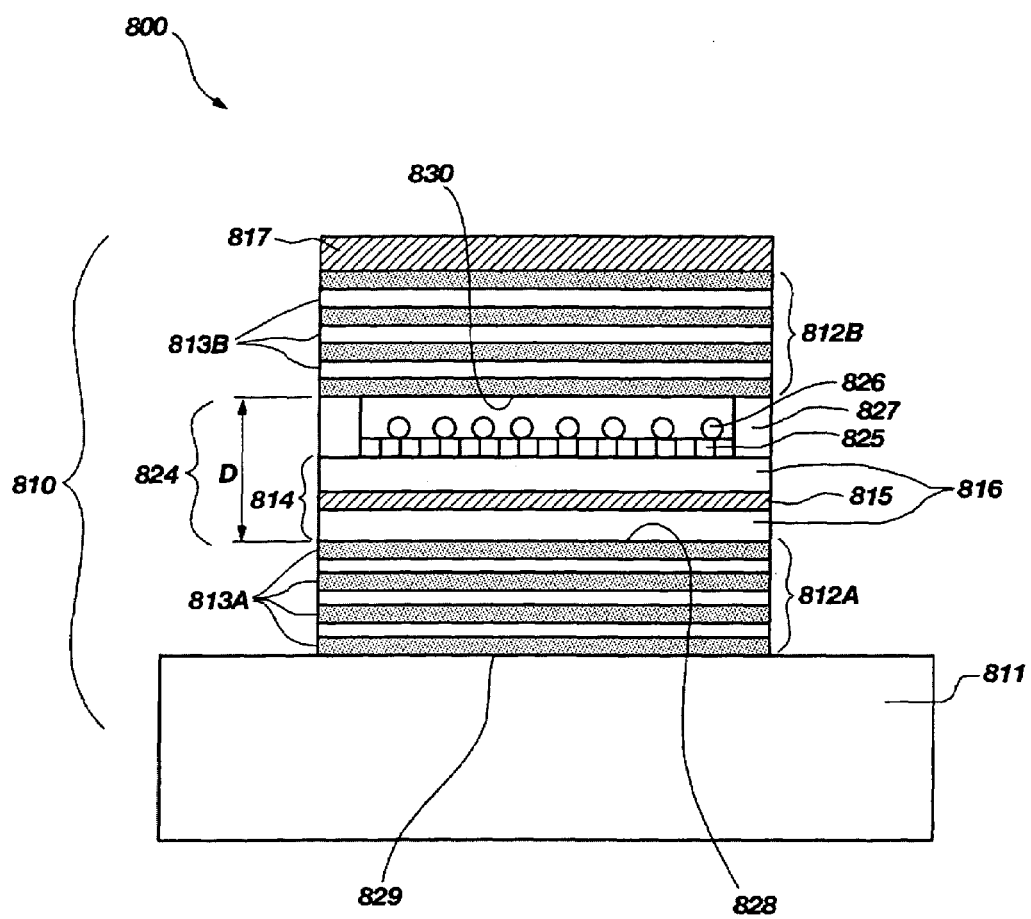
FIG. 8 is a sectional view of an exemplary integrated light source/amplifying structure.

An exemplary embodiment of an integrated light source/amplifying structure 800 is shown in FIG. 8. The integrated light source/amplifying structure 800 is a hybrid structure, having elements or features that function both as part of a radiation source and as part of a radiation amplifying structure, in contrast to the stacked integrated light source/amplifying structure 100 illustrated in FIG. 1A. The integrated light source/amplifying structure 800 includes a radiation source 810 that includes a substrate 811, a first Bragg mirror 812A, a second Bragg mirror 812B, an active region 814, and at least one electrical contact 817.

The first Bragg mirror 812A and the second Bragg mirror 812B may be identical in all respects to the first Bragg mirror 112A and the second Bragg mirror 112B of the integrated light source/amplifying structure 100 of FIG. 1B. The first Bragg mirror 812A has an upper surface 828 and a lower surface 829 that are generally parallel to each other. The second Bragg mirror 812B has a face 830 opposing the upper surface 828 of the first Bragg mirror 821A and is separated therefrom by a distance D.

The optical thicknesses of the low-index layers 813A and the high-index layers 813B may be selected to be approximately one-fourth the wavelength of the lasing light generated in the active region 814 of the integrated light source/amplifying structure 800 (e.g., having a thickness of $\lambda/4n$, where $\lambda$ is the wavelength of the incident light and n is the refractive index of the material).

The low-index layers 813A and the high-index layers 813B of the first Bragg mirror 812A and the second Bragg mirror 812B may be formed from any suitable semiconductor material. As an example, the layers may be formed from aluminum gallium arsenide having alternating concentrations of aluminum. Other examples of suitable material combinations for low-index layers 813A and high-index layers 813B include, but are not limited to: Si and $SiO_2$; GaN and GaAlN; and GaInAsP and InP. Many such suitable material pairs are known in the art and are intended to be included within the scope of the invention. In addition, the first Bragg mirror 812A and the second Bragg mirror 812B are alternatively doped with either a p-type dopant or an n-type dopant. As an example, the first Bragg mirror 812A may be n-type doped and the second Bragg mirror 812B may be p-type doped.

The active region 814, the region where the lasing light (i.e., the excitation radiation) is generated, may include a quantum well or active layer 815, and cladding layers 816. Additional quantum wells and cladding layers may be provided to improve the performance of the active area. The active layer 815 may be formed from doped gallium arsenide and the cladding layers 816 may be formed from undoped gallium arsenide. Each of the active layer 815 and the cladding layers 816 may be from about 50 angstroms to about 500 angstroms thick or thicker. It is not necessary that the thicknesses of the layers be equal.

The electrical contact 817 may be formed on the second Bragg mirror 812B, and may be formed from any suitable conductive material, including but not limited to gold, silver, copper, aluminum, or any other suitable metal or metal alloy, or a heavily doped semiconductor material. The electrical contact 817 may have a thickness between about 0.1 microns and about 5 microns.

The integrated light source/amplifying structure 800 may include a SERS-active structure 825 disposed adjacent the active region 814 between the first Bragg mirror 812A and the second Bragg mirror 812B. The SERS-active structure 825 enhances the Raman signal produced by photons from the excitation radiation that are inelastically scattered by the analyte 826 during analysis. The SERS-active structure 825 may be used to effect electromagnetic enhancement of the Raman signal, chemical enhancement of the Raman signal, or both. The representative SERS-active structure 825 illustrated in FIG. 1B comprises a mesh or screen formed from nanowires or rods having a diameter preferably less than about 20 nanometers.

Although the materials that form the SERS-active structure 825 typically are not transparent to the typical wavelengths of light used in Raman spectroscopy (about 350 nm to about 1000 nm), the SERS-active structure may be formed with apertures or spaces therethrough (such as the spaces between the nanospheres) to allow light to pass through the SERS-active structure 825.

Spacers 827 may be used to provide a certain amount of standoff between the SERS-active structure 825 and any adjacent layers, such as a cladding layer 816 or the second Bragg mirror 812B, and to allow an analyte 826 to diffuse or enter into the structure 800 through the lateral sides thereof. All structures of the integrated light source/amplifying structure 800 should be at least partially semiconductive or conductive such that current may pass through the device between the electrical contact 817 and the substrate 811 when a voltage is applied therebetween.

A resonant cavity 824 is defined by the region between the first Bragg mirror 812A and the second Bragg mirror 812B. The active region 814, the spacers 827, the SERS-active structure 825, and an analyte may be disposed within the resonant cavity 824, as shown in FIG. 8.

The integrated light source/amplifying structure 800 may be used to perform SERS by providing an analyte 826 within the structure 800 adjacent at least a portion of the SERS-active structure 825. A voltage may be applied between the electrical contact 817 and the substrate 811, causing current to flow through the device. As current passes through the active layer 815 of the active region 814, lasing light having certain wavelengths may be generated therein. If the distance D shown in FIG. 8 between the first Bragg mirror 812A and the second Bragg mirror 812B is an integer multiple of one half of the wavelength of a wavelength of lasing light generated in the active layer 815, that wavelength of radiation may be amplified within the resonant cavity 824.

The amplified excitation radiation will impinge on both the SERS-active structure 825 and the analyte 826 disposed adjacent the SERS-active structure near (or within) the resonant cavity 824. The irradiation of the SERS-active structure 825 by the amplified radiation produces a surface enhancement effect therein (i.e., chemical, electromagnetic, or both). In other words, irradiation of the SERS-active structure 825 by the amplified light may produce a strong electromagnetic field near the SERS-active structure 825.

The analyte 826 adjacent the portion of the SERS-active structure 825 that is being irradiated by the amplified radiation, in turn, experiences this very strong electromagnetic field. At least a portion of the amplified radiation may impinge on the analyte 826 and may be inelastically scattered as Stokes or anti-Stokes radiation (or both) to produce Raman scattered photons. The electromagnetic field enhances the intensity of the signal produced by Raman photons scattered by the analyte 826. Because the intensity of the Raman photons scattered by the analyte is, in part, proportional to the square of the electromagnetic field experienced by the analyte, the enhancement effect from the SERS-active structure may increase the intensity of the signal of the Raman scattered photons by as much as $10^{14}$.

Figure 9:
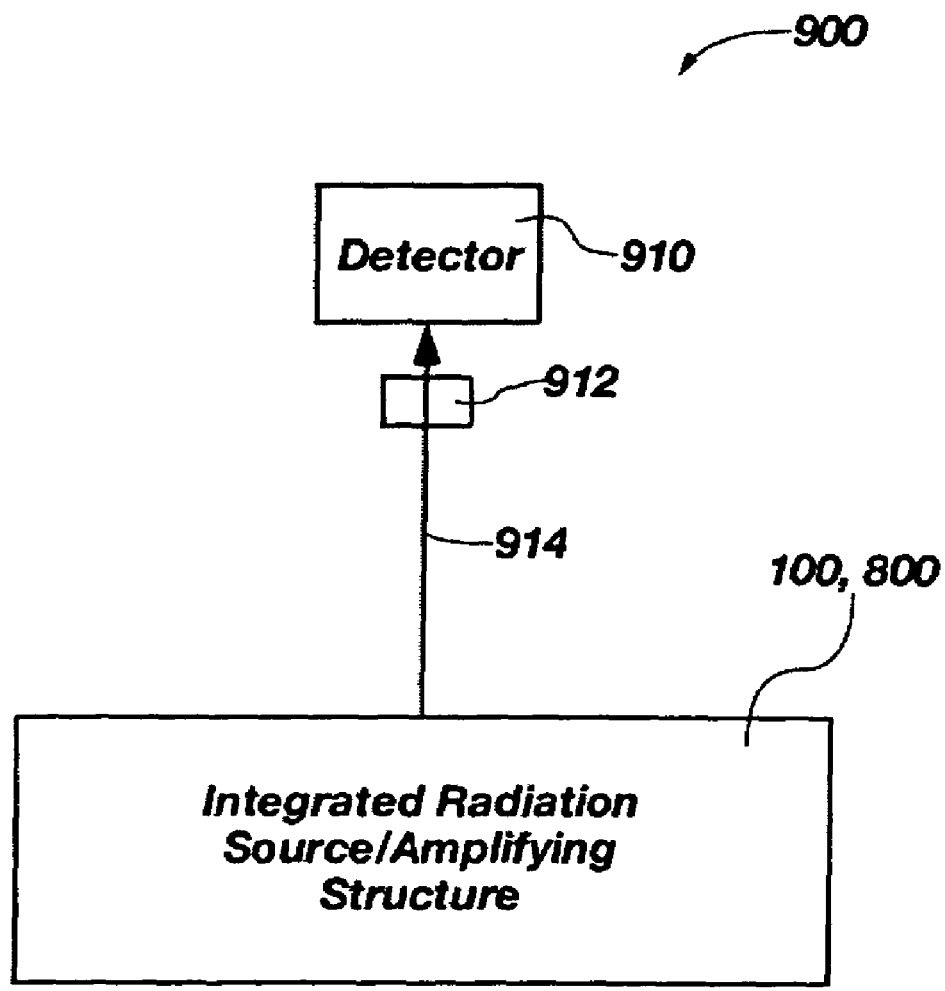
FIG. 9 is a simplified block diagram of an exemplary surface enhanced Raman spectroscopy (SERS) system employing an integrated light source/amplifying structure.

Referring to FIG. 9, a SERS system 900 includes an integrated radiation source/amplifying structure, such as integrated radiation source/amplifying structure 100 (FIG. 1B) or integrated radiation source/amplifying structure 800 (FIG. 8B), and a detector 910. The SERS system 900 may also include various optical components 912 between the integrated radiation source/amplifying structure and the detector 910.

The integrated radiation source/amplifying structure of the SERS system 900 will both generate excitation radiation and amplify the radiation. The amplified excitation radiation will impinge on both the SERS-active structure and the analyte disposed adjacent the SERS-active structure near or within the resonant cavity of the structure.

The Raman scattered photons 914 scattered by the analyte or sample may be collimated, filtered, or focused with optical components 912. For example, a filter or a plurality of filters may be employed, either included with the structure of the detector 910, or as a separate unit that is configured to filter the wavelength of the elastically scattered excitation radiation, thus, allowing only the Raman scattered photons 914 to be received by the detector 910.

The detector 910 receives and detects the Raman scattered photons 914 and may include a monochromator (or any other suitable device for determining the wavelength of the Raman scattered photons 914) and a device such as, for example, a photomultiplier for determining the quantity or number of the emitted Raman scattered photons (intensity).

Ideally, the Raman scattered photons 914 are isotropic, being scattered in all directions relative to the integrated radiation source/amplifying structure. Thus, the position of detector 910 relative to the structure is not particularly important.

Because the integrated radiation source/amplifying structure of the SERS system 900 integrates the excitation radiation source with the sample stage, and amplifies the excitation radiation impinging on the analyte, the SERS system 900 may be smaller and more portable compared to the relatively large conventional SERS systems. Furthermore, the SERS system 900 is capable of performing more sensitive chemical analysis (e.g., detection or analysis of single molecules) and consumes less power than conventional SERS systems as a result of the excitation radiation being amplified in the vicinity of the SERS-active structure and the analyte. The strength of the detected Raman signal is proportional to the intensity of the incident excitation radiation. Therefore, a stronger Raman signal from inelastically scattered photons can be generated and detected when using the structures and systems of the present invention as opposed to conventional SERS systems.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. An integrated radiation source/amplifying structure comprising:
    a first portion having a first surface and an opposing second surface;
    a second portion having a face opposing the first surface of the first portion with a resonant cavity provided therebetween;
    a SERS-active structure disposed between the first portion and the second portion within the resonant cavity; and
    a radiation source integrated with the SERS-active structure configured to irradiate the SERS-active structure.

2. The integrated radiation source/amplifying structure of claim 1, wherein at least one of the first portion and the second portion comprises a Bragg mirror.

3. The integrated radiation source/amplifying structure of claim 1, wherein at least one of the first portion and the second portion each comprise a two-dimensional photonic crystal.

4. The integrated radiation source/amplifying structure of claim 1, wherein at least one of the first portion and the second portion comprises a three-dimensional photonic crystal structure.

5. The integrated radiation source/amplifying structure of claim 4, wherein the three-dimensional photonic crystal structure comprises a plurality of layers, each layer of the plurality of layers including a two-dimensional photonic crystal.

6. The integrated radiation source/amplifying structure of claim 5, wherein at least one layer of the plurality of layers includes a defect in the two-dimensional photonic crystal.

7. The integrated radiation source/amplifying structure of claim 6, wherein the defect is located adjacent at least a portion of the SERS-active structure.

8. The integrated radiation source/amplifying structure of claim 1, wherein the SERS-active structure comprises a material selected from the group consisting of Au, Ag, Cu, Na, K, Cr, Al, and Li.

9. The integrated radiation source/amplifying structure of claim 1, wherein the SERS-active structure is located at a predetermined position between the first portion and the second portion within the resonant cavity.

10. The integrated radiation source/amplifying structure of claim 1, wherein the SERS-active structure comprises at least one nanowire having a diameter less than about 20 nanometers.

11. The integrated radiation source/amplifying structure of claim 1, further comprising spacer elements disposed between the first portion and the second portion.

12. The integrated radiation source/amplifying structure of claim 1, further comprising a cavity layer disposed between the first portion and the second portion, the cavity layer having a defect therein proximate the SERS-active structure.

13. The integrated radiation source/amplifying structure of claim 12, wherein the cavity layer comprises a first dielectric material.

14. The integrated radiation source/amplifying structure of claim 13, wherein the defect of the cavity layer comprises a second dielectric material, the refractive index of the second dielectric material being different than the refractive index of the first dielectric material.

15. The integrated radiation source/amplifying structure of claim 12, wherein the defect of the cavity layer includes a boundary, the boundary comprising a Bragg mirror.

16. The integrated radiation source/amplifying structure of claim 12, wherein the cavity layer comprises a two-dimensional photonic crystal, the two-dimensional photonic crystal exhibiting periodicity in refractive index in all directions parallel to the plane of the cavity layer.

17. The integrated radiation source/amplifying structure of claim 12, wherein one of the first portion and the second portion comprises an additional defect, the defect of the cavity layer and the additional defect together defining the resonant cavity of the integrated radiation source/amplifying structure.

18. The integrated radiation source/amplifying structure of claim 12, wherein the cavity layer and at least one of the first portion and the second portion are formed as a monolithic structure.

19. The integrated radiation source/amplifying structure of claim 1, wherein the radiation source comprises an active region disposed between the first portion and the second portion.

20. The integrated radiation source/amplifying structure of claim 19, wherein the active region comprises at least one quantum well.

21. The integrated radiation source/amplifying structure of claim 1, wherein the radiation source comprises a vertical cavity surface emitting laser (VCSEL).

22. The integrated radiation source/amplifying structure of claim 21, wherein the vertical cavity surface emitting laser (VCSEL) comprises:
    a first Bragg mirror;
    a second Bragg mirror; and
    at least one active region between the first Bragg mirror and the second Bragg mirror.

23. The integrated radiation source/amplifying structure of claim 22, wherein at least one of the first Bragg mirror and the second Bragg mirror is disposed adjacent at least one of the first portion and the second portion.

24. The integrated radiation source/amplifying structure of claim 23, wherein at least one of the first Bragg mirror and the second Bragg mirror is disposed adjacent a surface of at least one of the first portion and the second portion opposite the resonant cavity.

25. The integrated radiation source/amplifying structure of claim 1, wherein the first portion comprises a first Bragg mirror and the second portion comprises a second Bragg mirror.

26. The integrated radiation source/amplifying structure of claim 25, wherein the first Bragg mirror and the second Bragg mirror are separated by a distance approximately equal to an integer multiple of one half of a wavelength of radiation generated by the radiation source.

27. The integrated radiation source/amplifying structure of claim 1, wherein the resonant cavity comprises a resonant defect cavity in a photonic crystal.

28. The integrated radiation source/amplifying structure of claim 1, wherein the resonant cavity comprises a Fabry-Perot resonating cavity.

29. The integrated radiation source/amplifying structure of claim 1, wherein the radiation source integrated with the SERS-active structure comprises a surface enhanced Raman radiation having a wavelength about half of an impinging, excitation or pumping wavelength that can be observed.

30. A surface enhanced Raman spectroscopy (SERS) system, comprising:
   an integrated radiation source/amplifying structure comprising:
      a first portion having a first surface and an opposing second surface;
      a second portion having a face opposing the first surface of the first portion with a resonant cavity provided therebetween;
      a SERS-active structure disposed between the first portion and the second portion within the resonant cavity; and
      a radiation source integrated with the SERS-active structure and configured to irradiate at least a portion of the SERS-active structure; and
   a detector configured to receive Raman scattered light scattered by an analyte when the analyte is located within the resonant cavity and adjacent the SERS-active structure.

31. The SERS system of claim 30, wherein the radiation source comprises a vertical cavity surface emitting laser (VCSEL).

32. The SERS system of claim 30, further comprising optical components disposed between the integrated radiation source/amplifying structure and the detector.

33. Ther SERS system of claim 30, wherein the radiation source integrated with the SERS-active structure comprises a surface enhanced Raman radiation having a wavelength about half of an impinging, excitation or pumping wavelength that can be observed.

34. A method of performing surface enhanced Raman spectroscopy (SERS), comprising:
   providing an integrated radiation source/amplifying structure comprising:
      a first portion having a first surface and an opposing second surface;
      a second portion having a face opposing the first surface of the first portion with a resonant cavity provided therebetween;
      a SERS-active structure disposed between the first portion and the second portion within the resonant cavity; and
      a radiation source integrated with the SERS-active structure and configured to irradiate at least a portion of the SERS-active structure; and
   providing an analyte adjacent the SERS-active structure;
   generating excitation radiation from the radiation source;
   amplifying the excitation radiation within the resonant cavity, the amplified radiation impinging on at least a portion of the SERS-active structure and the analyte so as to effect Raman scattering of the amplified radiation by the analyte; and
   detecting the Raman scattered radiation.

35. The method of claim 34, wherein the integrated radiation source/amplifying structure comprises at least one of a Fabry-Perot resonant cavity, and a defect resonant cavity within a photonic crystal.

36. The method of claim 35, further comprising:
   selecting the wavelength of the excitation radiation to correspond to a resonance mode of the resonant cavity.

37. The method of claim 34, wherein detecting the Raman scattered radiation comprises: providing a detector configured to receive the Raman scattered radiation; and filtering radiation other than the Raman scattered radiation from the radiation being received by the detector.

38. The method of claim 34, wherein providing an analyte adjacent the SERS-active structure comprises placing the analyte adjacent the SERS-active structure.

39. The method of claim 34, wherein providing an analyte adjacent the SERS-active structure comprises diffusing the analyte onto the SERS-active structure.

40. The method of claim 34, wherein providing the radiation source integrated with the SERS-active structure comprises providing a surface enhanced Raman radiation having a wavelength about half of an impinging, excitation or pumping wavelength that can be observed.

* * * * *

UNITED STATES PATENT AND TRADEMARK OFFICE
CERTIFICATE OF CORRECTION

PATENT NO. : 7,177,021 B2
APPLICATION NO. : 10/942004
DATED : February 13, 2007
INVENTOR(S) : Shih-Yuan Wang et al.

It is certified that error appears in the above-identified patent and that said Letters Patent is hereby corrected as shown below:

In column 8, line 51, delete "FIG. 1A" and insert -- FIG. 10 A --, therefor.

In column 21, line 28, in Claim 33, delete "Ther" and insert -- The --, therefor.

Signed and Sealed this

Thirtieth Day of March, 2010

David J. Kappos
*Director of the United States Patent and Trademark Office*